Figure 1:
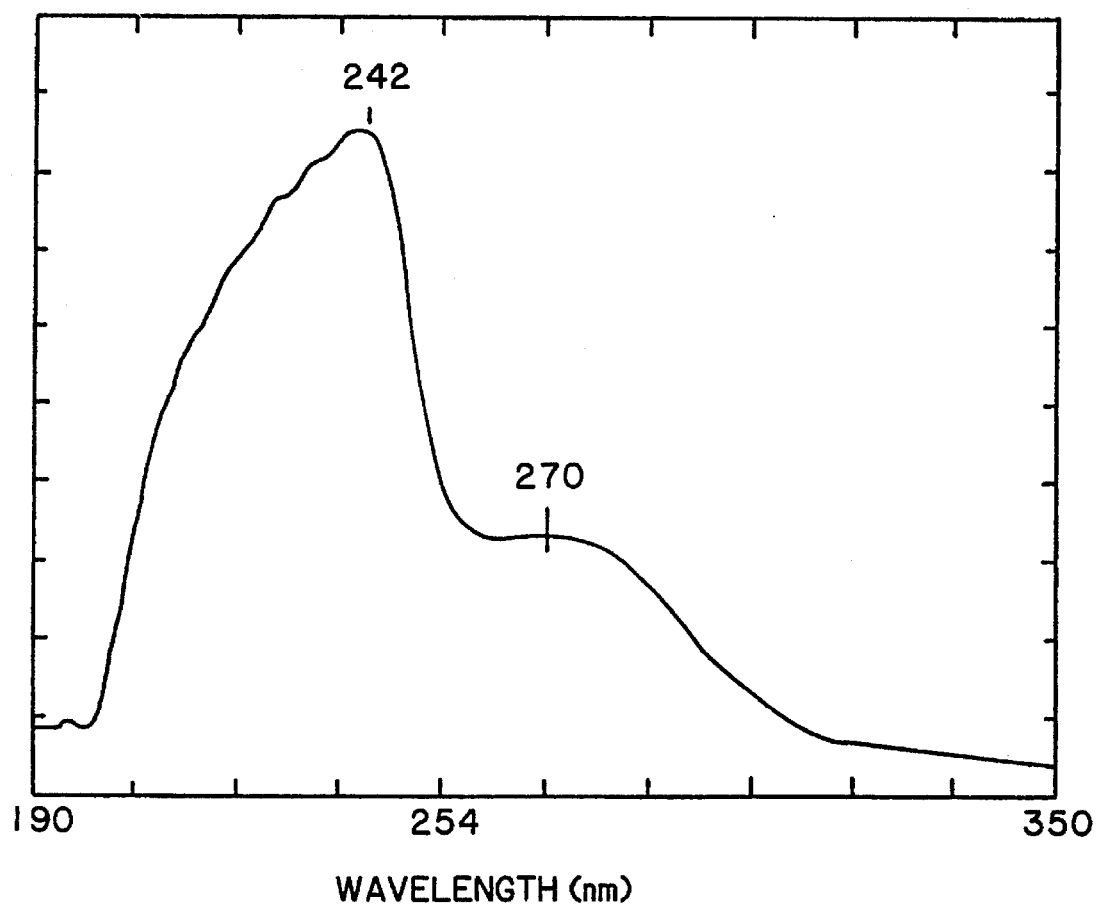

United States Patent [19]
Lee et al.

[11] Patent Number: 5,486,630
[45] Date of Patent: Jan. 23, 1996

[54] LEGIONELLA SPECIFIC ANTIBIOTIC

[75] Inventors: Yong W. Lee, Seoul; Yeong S. Lee, Goyang; Chang S. Yon, Seoul; Jung W. Suh, Inchun; Chul H. Lee, Seoul; Yoong H. Lim, Anyang; Ick D. Yoo, Daejeon, all of Rep. of Korea

[73] Assignees: Cheil Foods & Chemicals Inc., Seoul; Korea Institute of Science and Technology, Sungbuk-ku, both of Rep. of Korea

[21] Appl. No.: 340,358

[22] Filed: Nov. 14, 1994

[30] Foreign Application Priority Data

Sep. 14, 1994 [KR] Rep. of Korea ............... 94-23582
Sep. 14, 1994 [KR] Rep. of Korea ............... 94-23583
Sep. 14, 1994 [KR] Rep. of Korea ............... 94-23584

[51] Int. Cl.$^6$ .......... C07C 59/00; A01N 37/06; C12P 7/02; A61K 39/02
[52] U.S. Cl. .......... 554/1; 424/234.1; 435/155; 514/506; 514/546; 514/547; 514/549; 514/552
[58] Field of Search .......... 435/155; 424/234.1; 514/506, 546, 547, 549, 552; 554/1

[56] References Cited

U.S. PATENT DOCUMENTS 4,988,677 1/1991 Franco et al. .................. 514/30

*Primary Examiner*—David M. Naff
*Assistant Examiner*—Deborah K. Ware
*Attorney, Agent, or Firm*—Burns, Doane, Swecker & Mathis

[57] ABSTRACT

A Legionella specific antibiotic AL072 is disclosed. In addition the antibiotic is produced by the microorganism Streptomyces sp. AL91KCCM 10055. Further, the antibiotic compound has a specified formula.

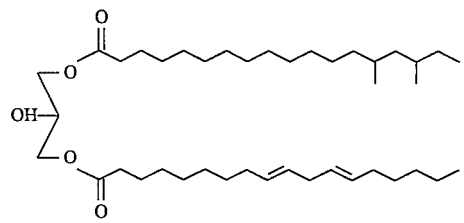

1 Claim, 5 Drawing Sheets

LEGIONELLA SPECIFIC ANTIBIOTIC

FIELD OF THE INVENTION

The present invention is directed to a novel Legionella specific antibiotic AL072, a novel Streptomyces sp. AL91 producing the same, and a process for producing the said antibiotic.

BACKGROUND OF THE INVENTION

*Legionella pneumophila,* which is the causal agent of Legionella infections, has been known to cause Legionnaires' disease or Pontiac fever. Since the bacteria was first isolated in Philadelpia, USA, it has been reported that many isolations of a species of Legionella were made from various patients and environments in all parts Of the world, including the USA, and 10 or more species were identified. *Legionella pneumophila* is one of the pathogens capable of causing pneumonia and it is presumed that 5% of the occurences of pneumonia are due to *Legionella pneumophila. Legionella pneumophila* grows in air-conditioning cooling towers, water service pipes, drain pipes, etc., and infections arc believed to occur in respiratory organs by inhalation of contaminated aerosols. In July, 1984, criticism was caused by the surprising fact that ill-defined symptoms of pneumonia which occurred in patients as well as medical teams at intensive care units of Koryo Hospital in Seoul appeared to be caused by Legionella species.

According to a result of investigation completed in 1985 by the National Health Institute, at least 90% of air-conditioning cooling towers within Seoul were contaminated with Legionella species and 93% of the isolated Legionella were identified as *Legionella pneumophila.* An additional investigation completed by the National Health Institute in major cities throughout the country, for example Seoul, Pusan, Daejeon, etc., between June and September, 1988 revealed that 83% of the isolated Legionella were classified to *Legionella pneumophila* serogroup 1.

Macrolide antibiotics, such as erythromycin, and quinolone antibiotics, such as rifampin, are known to be active against Legionella species and have been used for the treatment of the Legionella infections. However, these antibiotics have a wide spectrum of activity against a variety of microbes, in addition to the Legionella species. In this regard, an abuse of such antibiotics for extended periods may not only generate resistance to various microbes but also cause harmful problems such as the collapse of the balance of microbes occurring in a human body.

Additionally, there have been serious problems in that chemical agents for disinfecting air-conditioning cooling towers, which are contamination sources of Legionella species, may result in the contamination of the environment and the corrosion of the air-conditioning device.

Therefore, the development of novel Legionella specific antibiotics which are specifically active against only Legionella species, is needed and thereby may minimize the undesired problems. We have intensively investigated soil microbes over several years for the purpose of developing such antibiotics. Eventually, we succeeded in isolating a species of Streptomyces producing Legionella specific antibiotics and purifying a novel antibiotic specifically active against only Legionella species, which is designated Antibiotic AL072.

SUMMARY OF THE INVENTION

Cultivation of the novel microorganism Streptomyces sp. AL91 yields a novel antibiotic substance AL072 which is active exclusively against Legionella species, whose structure is represented as follows:

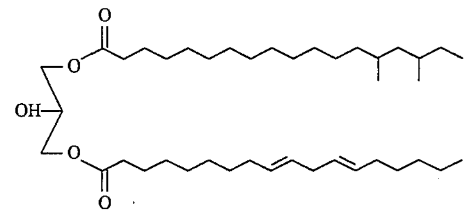

DESCRIPTION OF THE DRAWINGS

FIG. 1 shows the ultraviolet absorption spectrum of antibiotic substance AL072.

FIG. 2 shows the infrared absorption spectrum of antibiotic substance AL072.

FIG. 3 shows the mass spectrum of antibiotic substance AL072 measured by FAB/MS.

FIG. 4 shows the 400 MHz proton nuclear magnetic resonance spectrum of antibiotic substance AL072.

FIG. 5 shows the 100 MHz carbon nuclear magnetic resonance spectrum of antibiotic substance AL072.

DETAILED DESCRIPTION OF THE INVENTION

The Microorganism

The microorganism used for the production of Legionella specific antibiotic substance AL072 is Streptomyces sp. AL91. The microorganism was deposited at the permanent collection of the Korean Culture Center of Microorganisms, Seoul, Korea, on Jun. 2, 1994 under the Budapest Treaty on the international recognition of the deposit of microorganisms for the purposes of patent procedure, and a subculture of the organism can be obtained from the repository under the accession number KCCM 10055. In addition to the specific microorganism described and characterized herein, it should be understood that mutants of the microorganism (e.g., mutants produced through the use of X-ray, ultraviolet radiation or nitrogen mustards) can also be cultivated to produce the antibiotic substance AL072.

Isolation of Streptomyces sp. AL91 was accomplished by shaking 1.0 g of dried soil sample in 10 ml of sterile distilled water, plating 0.1 ml of dilutions of the soil suspension on a Humic acid-Vitamin agar supplemented with Cycloheximide (50 μg/ml) and Nalidixic acid (200 μg/ml), and cultivating the plate at the temperature of 28° C. for 14–21 days. The medium was sterilized at 121° C. for 15 minutes before the antifungal agent Cycloheximide and the antibacterial agent Nalidixic acid, seperately sterilzed by filtration, were added. The composition of Humic acid-Vitamin agar is described in Table I.

TABLE I

| | |
|---|---|
| Humic acid<br>(dissolved in 10 ml of 0.2 N NaOH) | 1.0 g |
| $Na_2HPO_4$ | 0.5 g |
| KCl | 1.71 g |
| $MgSO_4.7H_2O$ | 0.05 g |
| $FeSO_4.7H_2O$ | 0.01 g |
| Thiamin-HCl | 0.5 mg |
| Vitamin $B_2$ | 0.5 mg |
| Niacin | 0.5 mg |

TABLE I-continued

| | |
|---|---|
| Pyridoxine-HCl | 0.5 mg |
| Inositol | 0.5 mg |
| Pantothenic Acid Ca-salt | 0.5 mg |
| p-Aminobenzoic Acid | 0.5 mg |
| Biotin | 0.25 mg |
| Cycloheximide | 50 mg |
| Nalidixic acid | 200 g/mL |
| Agar | 20 g |
| Distilled water (pH 7.0) | 1 L |

Characteristics of Streptomyces sp. AL91 KCCM 10055

Morphology: Spores are formed by spiral, branched chains. The surface of spores is smooth.

Biochemical characteristics: The ability to liquefy gelatin is negative and the ability to degrade starch is positive.

Cultural characteristics:

| Media | Growth | Color of aerial mycelium | Reverse color | Soluble pigments |
|---|---|---|---|---|
| Trypton-yeast extract agar | good | brown | brown | brown |
| Yeast extract-malt extract agar | good | white | brown | — |
| Oat meal extract agar | good | pale orange or white | — | — |
| Inorganic salt-starch agar | good | white | — | — |
| Glycerol-asparagine agar | good | dense yellow | dense yellow | — |
| Peptone-yeast extract-iron agar | poor | dense brown | brown | dense brown |
| Tyrosine agar | good | white-brown | dense brown | — |
| Bennett' medium | good | white | yellow-brown | — |

Carbon utilization:

Positive: D-Glucose, sucrose, D-xylose, D-mannitol, D-fructose, rhamnose, raffinose, cellulose.

Negative: L-Arabinose, I-inositol.

Susceptibility to antibiotics:

| antibiotics | Concentrations (μg/mL) | Size of ring occurred by inhibition of growth (mm, in diameter) |
|---|---|---|
| Carbenicillin | 100 | — |
| Chloramphenicol | 30 | 27.7 |
| Neomycin | 30 | 12.0 |
| Nalidixic acid | 30 | — |
| Vancomycin | 30 | 22.0 |
| Clindamycin | 2 | — |
| Ampicillin | 10 | 12.0 |
| Kanamycin | 30 | 17.0 |
| Tetracycline | 30 | 17.0 |
| Cephalothin | 30 | 24.0 |
| Erythromycin | 15 | 40.0 |
| Rifampin | 5 | — |
| Gentamycin | 10 | 10.0 |
| Streptomycin | 10 | 17.0 |

Production of the Antibiotic substance AL072

Streptomyces sp. AL91 KCCM 10055 was grown on a nutrient agar containing the components listed in Table II for 3 days. The cultures were inoculated into 200 mL of a liquid medium containing the components listed in Table III and cultivated at the temperature of 28° C. under aerobic conditions for 3 days. Subsequently, the culture solution was inoculated into 6 L of a liquid medium containing the components listed in Table IV and cultivated at the temperature of 28° C. under aerobic conditions for 5 days. The antibiotic AL072 was isolated and purified from the final culture solution by the procedures described below.

TABLE II

| | |
|---|---|
| Sucrose | 20.0 g |
| Glucose | 10.0 g |
| Corn steep liquor | 5 mg |
| Yeast extracts | 4.9 g |
| Soybean flour | 20.0 g |
| $CaCO_3$ | 4.0 g |
| NaCl | 2.0 g |
| $K_2HPO_4$ | 0.05 g |
| Agar | 15 g |
| Distilled water (pH 7.3) | 1 L |

TABLE III

| | |
|---|---|
| Glucose | 1 g |
| Soluble starch | 24 g |
| Peptone | 3 g |
| Malt extract | 5 g |
| $CaCO_3$ | 4 g |
| Distilled water (pH 7.0) | 1 L |

TABLE IV

| | |
|---|---|
| Sucrose | 20.0 g |
| Glucose | 10.0 g |
| Corn steep liquor | 5 mL |
| Yeast extract | 4.9 g |
| Soybean flour | 20.0 g |
| $CaCO_3$ | 4.0 g |
| NaCl | 2.0 g |
| $K_2HPO_4$ | 0.05 g |
| Distilled water (pH 7.3) | 1 L |

After cultivation was completed, 6 L of the culture solution was mixed with an equivalent amount of isopropyl alcohol by stirring. After standing over night, the mixture was centrifuged and the resulting supernatant was taken. The supernatant was tilted through the passage of diatomaceous earth and the filtrate was then concentrated under reduced pressure to remove the isopropyl alcohol. The resulting concentrate was three times extracted with ethylacetate, which was then removed under reduced pressure. The residue was dissolved in 50% isopropyl alcohol and the resulting solution was then concentrated under reduced pressure to remove the isopropyl alcohol. The residual aqueous solution was passed on a column filled with octadecyl silica gel and the passed solution was discarded. Legionella specific antibiotics adhered to the ODS resin were eluted with 70% ethyl alcohol and the elutes were then concentrated under reduced pressure to dryness. After the dried concentrates were dissolved in 80% isopropyl alcohol, preparative high pressure liquid chromatography (206 nm) on silica gel, eluting with acetonitrile-distilled water, 68:32 at the rate of 30 mL/min, gave crude Leginella specific antibiotic substance AL072. Subsequently, the crude antibiotics were concentrated under a reduced pressure to dryness, the dried concentrates were dissolved in 50% isopropyl and the resulting solution was again concentrated under reduced pressure. The isopropyl alcohol was removed and the residue was three times extracted with chloroform. The chloroform was removed and the residue was dissolved in 80% isopropyl alcohol. High pressure liquid chromatography, run in the same conditions as used in the first chromatography, gave pure antibiotic AL072.

Physico-chemical properties of Antibiotic substance AL072

1. Thin-layer chromatography was conducted on Merck & Co. No. 5642 HPTLC silica gel plate with the development of chloroform-methyl alcohol, 19:1. Antibiotic AL072 samples were spotted on the silica gel plate and developed in a sealed container. After development, an aqueous 10% sulfuric acid solution containing 5% ammonium molybdate and ceric ammonium sulfate was sprayed on the silica gel plate which was then heated to 100° C. for 10 minutes to develop a colour. As a result of this, the Rf value of antibiotic AL072 was 0.58.

2. Antibiotic AL072 is soluble in alcohols such as methyl alcohol, ethyl alcohol, isopropyl alcohol, etc., and organic solvents such as ethyl acetate, chloroform, etc., whereas it is not or poorly soluble in water.

3. Antibiotic AL072 is very stable in aqueous solutions with pH values between pH 2 and pH 12. The activity of antibiotic AL072 is unchanged by heat of 95° C. for 1 hour.

Figure 2:
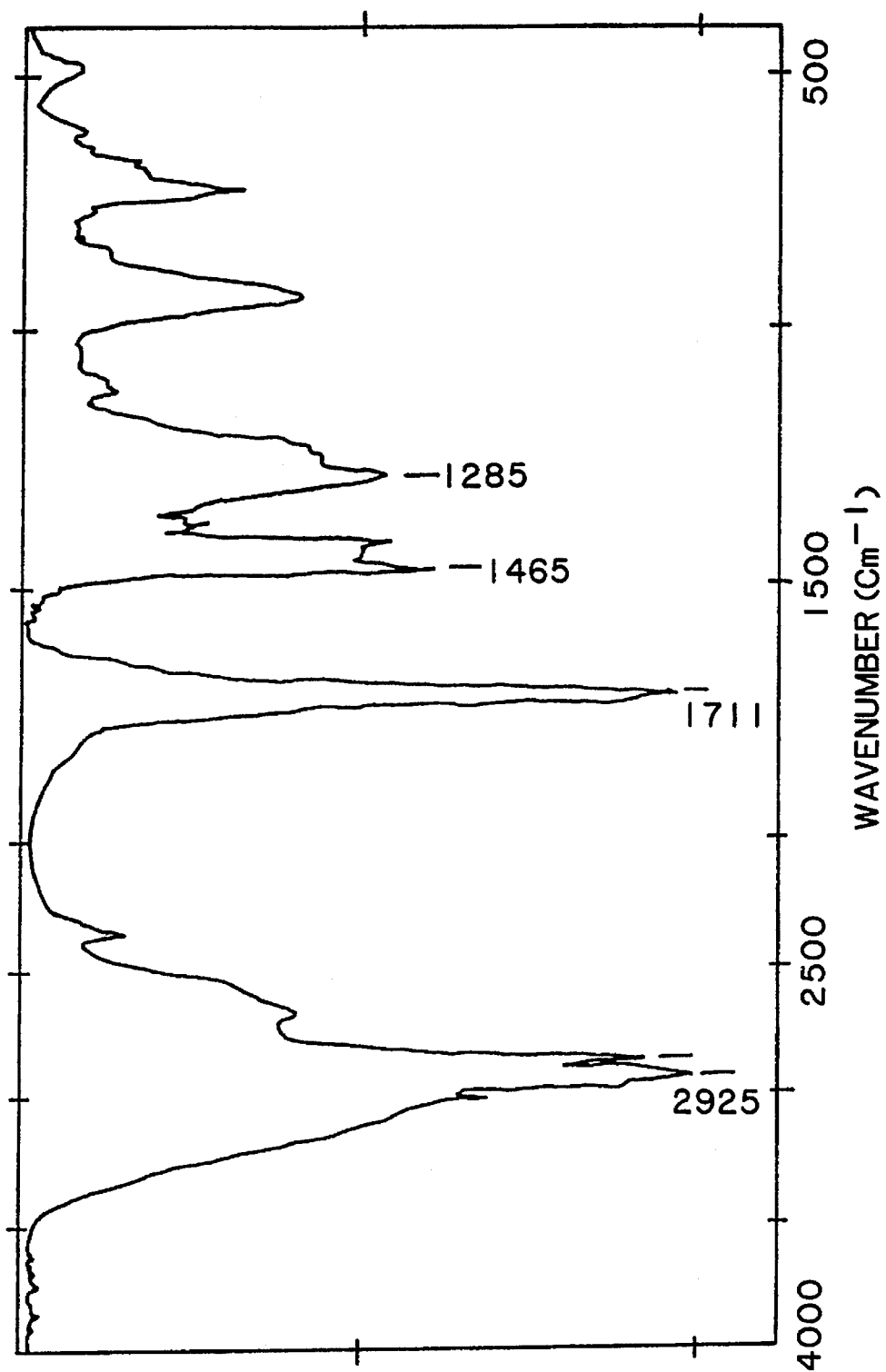
Figure 3:
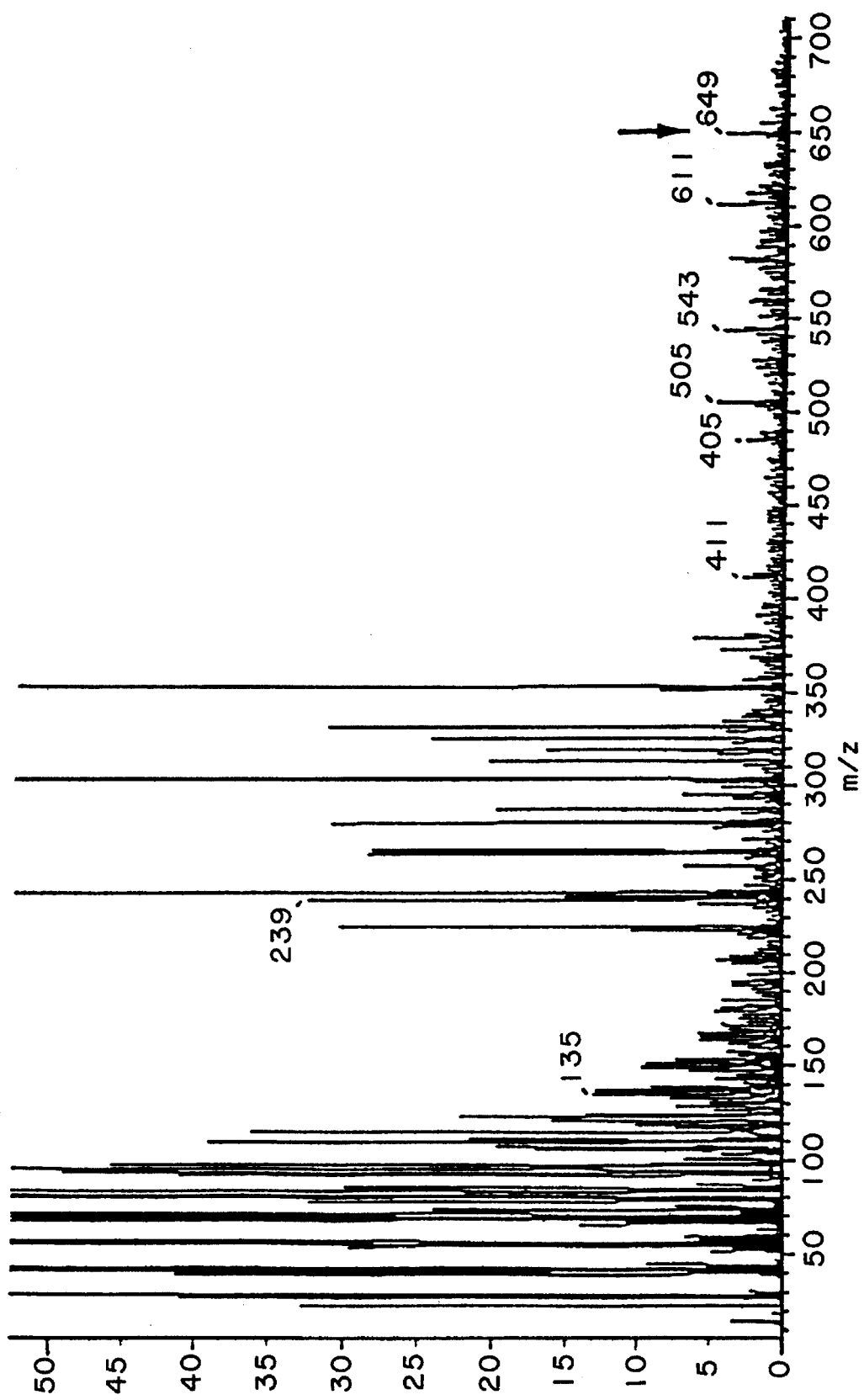

4. As a result of ultraviolet spectrometry, antibiotic AL072 in methyl alcohol is shown to have a maximum absorption in 242 nm (FIG. 1). 5. The infrared absorption spectrum of antibiotic AL072 in potassium bromide using Bruker FT-IR spectrometer is shown in FIG. 2.

Figure 4:
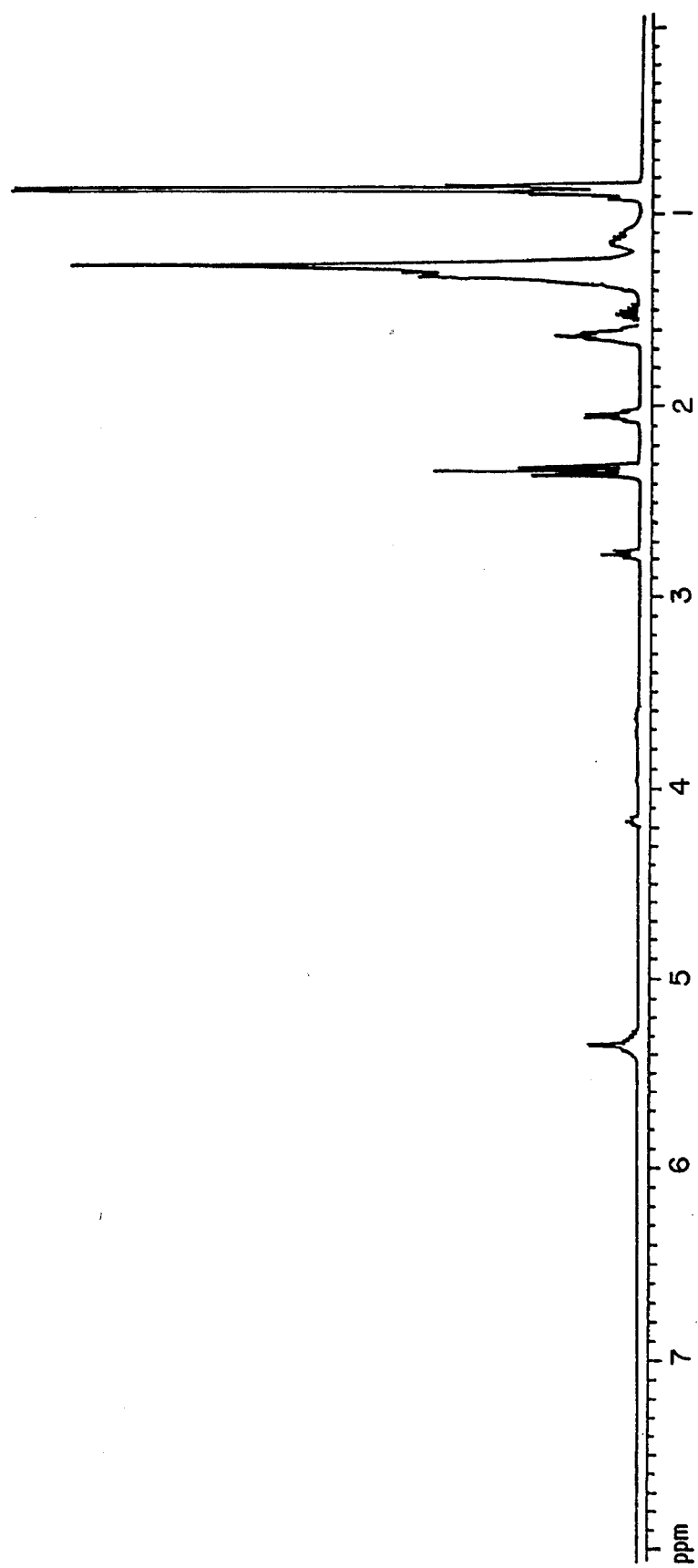

6. The proton nuclear magnetic resonance spectrum of antibiotic AL072 in $CDCl_3$ using Bruker ARX400 spectrometer is shown in FIG. 4. H-NMR $\delta$ (400 MHz):0.86(3H,m); 0.87(3H,m); 0.88(3H,m); 0.91(3H,m); 1.29(43H,m); 1.61(4H,m); 2.03(2H,m); 2.31(4H,m); 2.75(1H,m); 3.62(1H, dd, 12 Hz, 6 Hz); 3.72(1H, dd, 4 Hz, 12 Hz); 3.96(1H,m); 4.14(2H,m); 5.35(4H,m) ppm.

Figure 5:
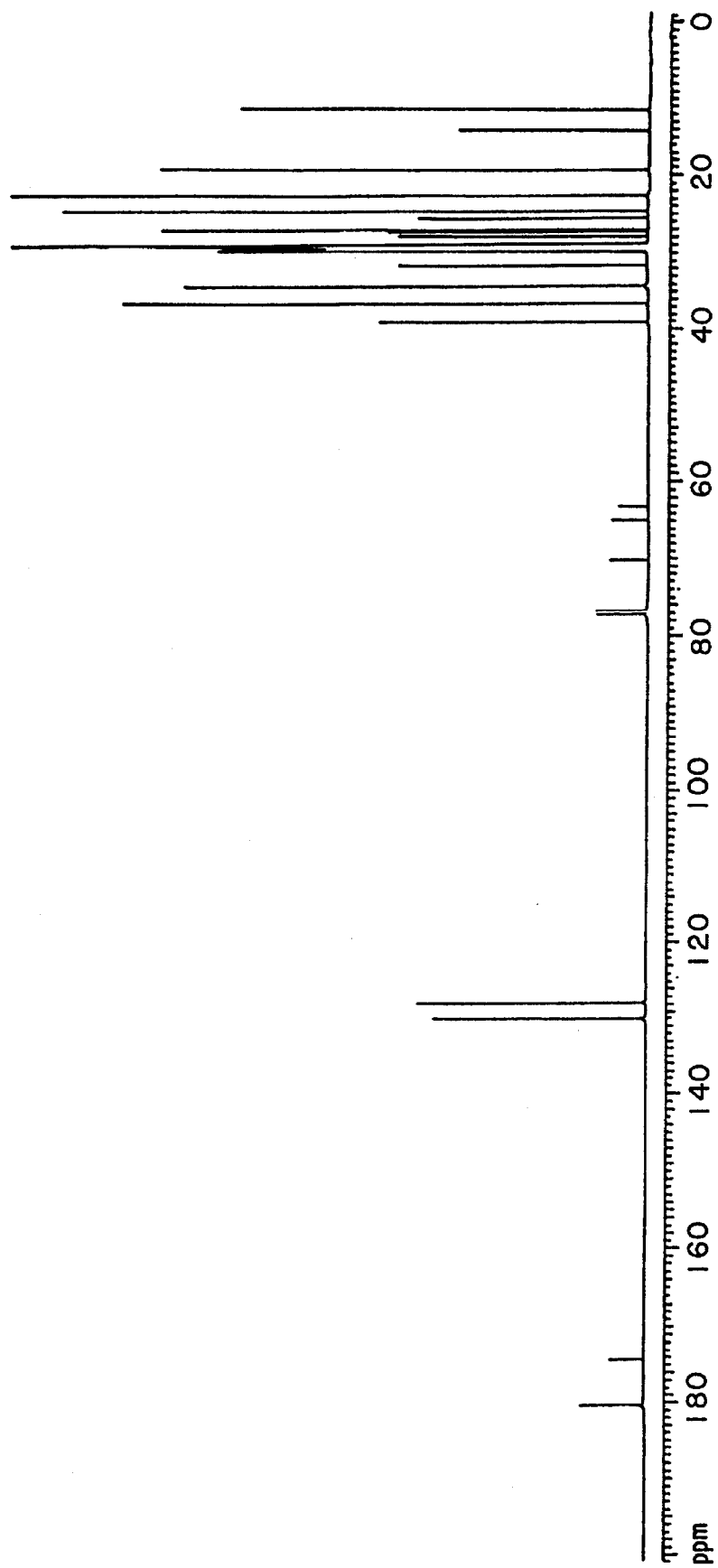

7. The carbon nuclear magnetic resonance spectrum of antibiotic AL072 in $CDCl_3$ using Bruker ARX400 spectrometer is shown in FIG. 5. C-NMR $\delta$ (100 MHz): 12.01(q); 14.67(q); 19.85(q); 23.23(q); 23.28(q); 25.34(t); 25.36(t); 26.29(t); 27.78(t); 27.84(t); 27.87(t); 28.10(t); 28.63(d); 29.72(t); 29.75(t); 29.82(t); 29.93(t); 30.02(t); 30.17(t); 30.26(t); 30.29(t); 30.33(t);30.36(t); 30.38(t); 30.62(t); 30.69(t); 32.20(t); 34.79(t); 34.81(t); 35.08(d); 37.33(t); 39.75(t); 63.90(t); 65.95(t); 70.96(d); 128.50(d); 128.70(d); 130.60(d); 130.70(d); 174.90(s); 181.00(s) ppm.

Biological Activity of Antibiotic substance AL072

The effects of antibiotic substance AL072 obtained according to the above procedures on growth of various microbes were shown in Table V below. It is evident that while the antibiotic substance AL072 is powerfully active against *Legionella pneumophila*, it is not or only slightly active against the other microbes tested.

TABLE V

| Microorganism | Diameter of ring produced by inhibition of growth (mm) |
|---|---|
| *Legionella pneumophila* ATCC 33152 | 108 |
| *Staphylococcus aureus* | 11 |
| *Streptococcus pyogenes* | — |
| *Streptococcus* | 20 |
| *Streptococcus agalactiae* | — |
| *Streptococcus equi* | 21 |
| *Streptococcus durans* | 24 |
| *Listeria monocytogenes* | 12 |
| *Corynebacterium diphtheriae* | 9 |
| *Bacillus subtilis* | 8 |
| *Bacillus megaterium* | 6 |
| *Escherichia coli* | 6 |
| *Citrobacter freundii* | — |
| *Salmonella typhimurium* | 14 |
| *Shigella flexneri* | — |
| *Klebsiella pneumoniae* | — |
| *Klebsiella oxytoca* | — |
| *Klebsiella aerogenes* | — |
| *Enterobacter cloacae* | — |
| *Enterobacter aerogenes* | 9 |
| *Serratia marcescens* | — |
| *Proteus mirabilis* | — |
| *Proteus vulgaris* | 12 |
| *Proteus rettgeri* | — |
| *Proteus morgani* | — |
| *Pseudomonas aeruginosa* | — |
| *Pseudomonas cepacia* | — |

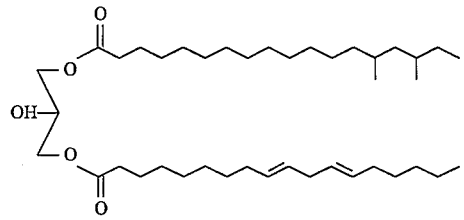

What is claimed is:
1. A compound of the formula: